US00PP11272P

United States Patent [19]

Segers

[11] Patent Number: Plant 11,272

[45] Date of Patent: Mar. 7, 2000

[54] HYBRID TEA ROSE PLANT NAMED 'PRETANER'

[75] Inventor: Theodorus A. Segers, Hoofddorp, Netherlands

[73] Assignee: Pregro Royalty B.V., NaaldWijk, Netherlands

[21] Appl. No.: 08/929,942

[22] Filed: Sep. 15, 1997

[51] Int. Cl.[7] ..... A01H 5/00

[52] U.S. Cl. ..... Plt./134

[58] Field of Search ..... Plt./14, 15, 134, Plt./133, 145, 144

*Primary Examiner*—Howard J. Locker
*Attorney, Agent, or Firm*—C. A. Whealy

[57] ABSTRACT

A distinct cultivar hybrid tea of rose plant named 'Pretaner', characterized by its large light yellow to white flowers; freely branching plant habit; long stem length; and excellent postproduction longevity.

1 Drawing Sheet

The present invention relates to a new and distinct cultivar of hybrid tea rose plant, botanically known as Rosa hybrida, commercially used as a cut flower, and hereinafter referred to by the cultivar name 'Pretaner'.

The new cultivar is a product of a planned breeding program conducted by the inventor in Rijsenhout, The Netherlands. The objective of the breeding program was to develop cut rose varieties with novel and attractive flower colors, numerous flowering stems per plant, and good post-production longevity. The new cultivar originated from a cross made by the inventor in 1991 of two proprietary seedlings. The proprietary selection P23 was the female, or seed, parent, and the proprietary selection 90-81 was the male, or pollen, parent. The cultivar Pretaner was discovered and selected by the inventor as a flowering plant within the progeny of the stated cross in a controlled environment in Rijsenhout, The Netherlands.

Asexual propagation of the new cultivar by cuttings taken at Rijsenhout, The Netherlands, has shown that the unique features of this new rose plant are stable and reproduced true to type in successive generations.

The following traits have been repeatedly observed and are determined to be the unique characteristics of 'Pretaner'. These characteristics in combination distinguish the new rose plant as a new and distinct cultivar:

1. Large light yellow to white flowers.
2. Freely branching with numerous flowering stems per plant.
3. Long stem length.
4. Excellent postproduction longevity.

The new rose plant has not been observed under all possible environmental conditions. The phenotype may vary significantly with variations in environment such as temperature, light or fertility level, without, however, any variance in genotype.

BRIEF DESCRIPTION OF PHOTOGRAPH

The accompanying colored photograph illustrates the new rose plant, showing the colors as true as it is reasonably possible to obtain in colored reproductions of this type. The photograph comprises a top perspective view of typical flowering stems of the new rose plant grown in Rijsenhout, The Netherlands. Flower and foliage color in these photographs may appear different from the actual colors due to light reflectance.

DETAILED BOTANICAL DESCRIPTION

The following observations, measurements, values, and comparisons describe plants grown in Rijsenhout, The Netherlands, under glass with average day temperatures of 19° C. and average night temperatures of 17° C.

In the following description, color references are made to The Royal Horticultural Society Colour Chart except where general terms of ordinary dictionary significance are used.

Classification:

*Botanical.*—Rosa hybrida cultivar Pretaner.

*Commercial.*—Cut rose.

Parentage:

*Male or pollen parent.*—Rosa hybrida proprietary selection 90-81.

*Female or seed parent.*—Rosa hybrida proprietary selection P23.

Propagation:

*Type.*—Cuttings.

*Time to initiate roots.13* About 12 days with soil temperatures of 25° C.

*Time to develop roots.*—About 25 days with soil temperatures of 25° C.

*Rooting habit.*—Fine, fibrous and well-branched.

Plant description:

*Form.*—Upright.

*Growth habit.*—Moderately vigorous. Freely branching and dense growth.

*Plant size.*—About 110 cm in height and about 40 cm in width.

*Productivity.*—About 190 stems per square meter per year under greenhouse year-round production.

*Stem and lateral branches.*—Quantity of lateral branches: Typically four. Length of lateral branches: About 90 cm. Internode length: About 8 cm. Color: 137B . Prickles: Present, moderate in number. Length: About 1 cm. Color: Apex: 200D. Base: 194B.

*Foliage description.*—Leaves arranged alternately, compound with three, five, seven or nine leaflets per leaf, and generally symmetrical. Of the apical 12 compound leaves, typically the distal leaf has three leaflets, the next three leaves have five leaflets, the next six leaves have seven leaflets, and the proximal two leaves have nine leaflets. Quantity of leaves: About 12 per lateral branch. Length, nine-leaflet leaf: About 19 cm. Width, nine-leaflet leaf: About 16 cm. Length of leaflet of seven-leaflet leaf: About 7.6 cm. Width of leaflet of seven-leaflet leaf: About 5.7 cm. Length of leaflet of nine-leaflet leaf: About 8.9 cm. Width of leaflet of nine-leaflet leaf: About 6.2 cm.

Shape: Ovate with acute apex and obtuse base. Margin: Serrate. Texture: Smooth and glossy. Petiole length: About 3.5 cm. Petiole diameter: About 2 mm. Stipule: Foliaceous, adnate to petiole. Color: Young foliage, upper side: 147A. Young foliage, under side: 200D. Mature foliage, upper side: 135A. Mature foliage, under side: 146B. Venation, upper side: 135A. Venation, under side: 146B. Petiole: 136A.

Flower description:

*Flower type and habit.*—Large light yellow to white flowers. Consistently symmetrical rosette flowers. Freely and continuous flowering. Flowers borne singly at terminal apices or in clusters of up to three each. Flowers persistent.

*Flowering season.*—Year-round under greenhouse conditions.

*Rate of flower opening.*—About 10 days.

*Fragrance.*—Faint pleasant, typical of Rosa.

*Flower diameter.*—About 12.5 cm.

*Flower depth (height).*—About 7 cm.

*Flower longevity on plant.*—About 20 days.

*Flower longevity as a cut flower.*—About 18 days.

*Flower buds.*—Shape: Ovate. Length: About 5.8 cm. Diameter: About 4 cm. Color: 15B.

*Petals/petaloids.*—Quantity: About 44 per flower. Typically about five rows with about nine petals each. Length: About 6.5 cm. Width: about 6.8 cm. Shape: Rounded with mucronate apex. Aspect: Petals reflex as the flowers open. Margin: Undulate and entire. Texture: Satiny and slightly rippled. Color: Upper side, when opening: Center of petal, 16D/13D; outer margin, 11D; apex, 155A ; outer petals occasionally have green streaks. Under side, when opening: Center of petal, 16C/13D; outer margin; 11D; apex, 155A, Upper side, fully opened: center of petal, 16D/13D; outer margin, llD; apex, 155A, outer petals occasionally have green streaks. Under side, fully opened: Center of petal, 16C/13D; outer margin, 11D; apex, 155A. Fading to: 155A.

*Sepals.*—Quantity: Typically five per flower. Calyx length: About 4.8 cm. Calyx width: About 4.6 cm. Shape: Subulate with aristate tip. Color: Upper side: 139A. Under side: 146A.

*Peduncles.*—Strength: Very strong. Aspect: Erect. Texture: Smooth. Length: About 9.5 cm. Color: 137C.

*Reproductive organs.*—Stamens: Quantity: About 75 per flower. Anther size: Length, about 3.5 mm and width, About 0.8 mm. Anther shape: Ovate. Anther color: 13A. Pollen: Moderate, 10B in color. Pistils: Quantity: About 103 per flower. Pistil length: About 1.1 cm. Style color: 155B/181A. Stigma color: 5C. Ovary color: 155B.

Seed description:

*Length.*—About 7 mm.

*Width.*—About 4.5 mm.

*Color.*—159A.

Disease resistance: Moderate resistance to Powdery Mildrew has been observed under commerical greenhouse production conditions.

It is claimed:

1. A new and distinct rose plant named 'Pretaner', as illustrated and described.

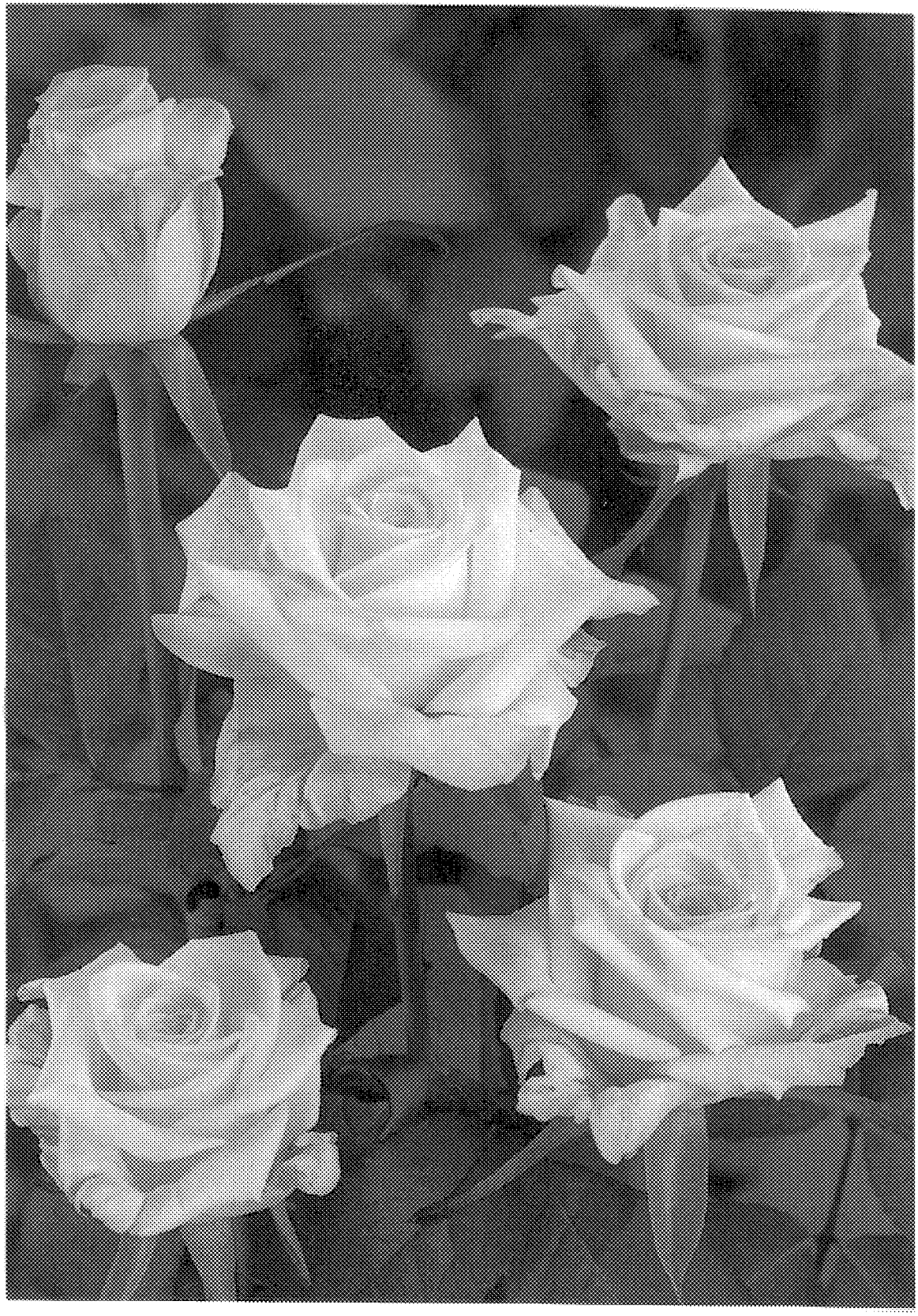

* * * * *